United States Patent [19]

Hawthorne et al.

[11] 4,363,747

[45] Dec. 14, 1982

[54] METALLOCARBORANE PRECURSOR AND CATALYST

[75] Inventors: M. Frederick Hawthorne, Encino, Calif.; Mark S. Delaney, Midland, Mich.

[73] Assignee: The Regents of the University of California, Berkeley, Calif.

[21] Appl. No.: 273,731

[22] Filed: Jun. 15, 1981

[51] Int. Cl.³ .................. B01J 31/12; C07F 15/00
[52] U.S. Cl. ....................... 252/431 P; 260/429 R
[58] Field of Search ................ 260/429 R; 252/431 P

[56] References Cited

U.S. PATENT DOCUMENTS 3,976,596  8/1976  Hawthorne et al. ............ 252/431 P
4,062,883  12/1977  Hawthorne et al. ............ 260/429 R Primary Examiner—Helen M. S. Sneed
Attorney, Agent, or Firm—Poms, Smith, Lande & Rose

[57] ABSTRACT

An extraordinarily active carborane catalyst for use in hydrogenation, hydroformulation and isomerization reactions. The new catalyst is a modification of known metallocarborane catalysts having a transition metal symmetrically bonded to the pentagonal face of a dicarborane cage with two triphenylphosphine ligands and one hydrogen ligand occupying the remaining transition metal ligand sites. The new alkene-metallocarborane replaces one of the triphenylphosphine ligands with a lower chelating or bridging alkene which is bound to both the transition metal and the carborane cage.

The alkene-metallocarborane catalyst may be used as a homogenous catalyst or may be bound to a suitable polymer support for use as a heterogeneous catalyst. The catalyst has been found to be among the most highly reactive catalysts known to date. It is believed the high reactivity of the new catalyst is due to the in situ irreversible hydrogenation of the alkene side chain to produce an open coordination site on the transition metal atom.

8 Claims, 1 Drawing Figure

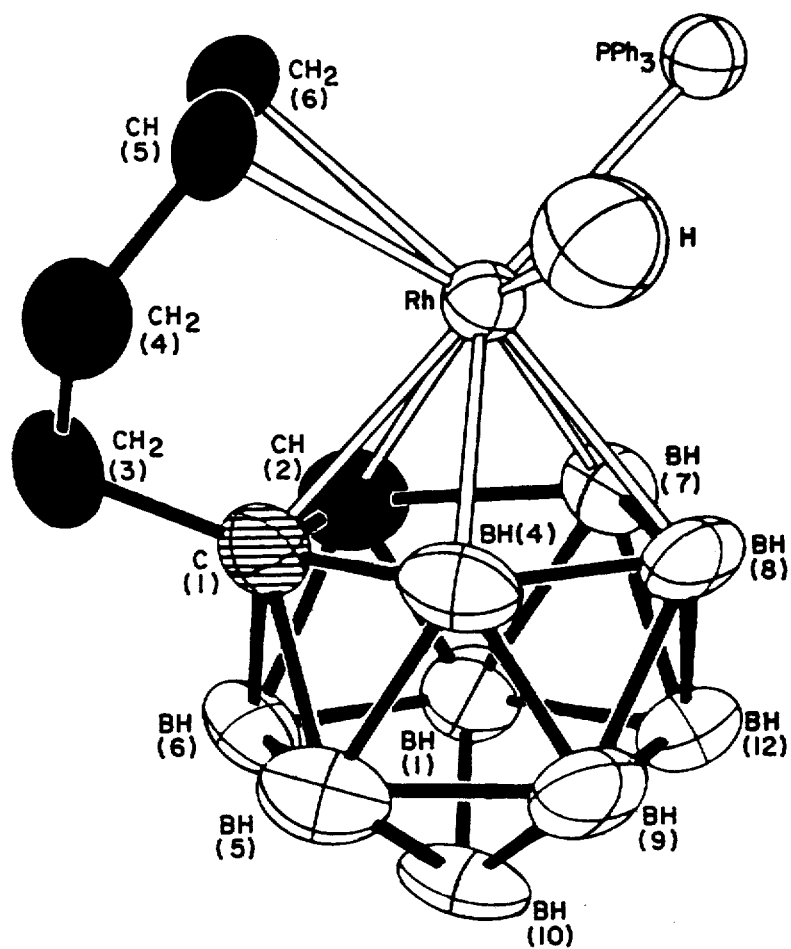

METALLOCARBORANE PRECURSOR AND CATALYST

The government has rights in this invention pursuant to Contract No. N00014-76-C-0390 awarded by the Department of the Navy and Grant No. CHE78-05679 awarded by the National Science Foundation.

BACKGROUND OF THE INVENTION

The present invention relates generally to metallocarborane compounds which are useful as hydrogenation, hydroformylation and isomerization catalysts. More particularly, the present invention relates to the discovery of an extraordinarily active metallocarborane catalyst.

In recent years, the discovery and utility of homogenous and heterogenous hydrogenation, hydroformylation and isomerization catalysts have expanded in scope to become one of the largest areas of endeavor in organic chemistry. Among the more promising catalysts are those catalysts based on metallocarborane compounds. In U.S. Pat. No. 3,976,596, issued to Hawthorne et al. on Aug. 24, 1976, the discovery of a family of stable metallocarboranes based on rhodium and iridium were first described as being effective catalysts for the homogenous hydrogenation, isomerization and hydroformylation of olefins and the hydrosilation of ketones. The metallocarborane catalyst disclosed in U.S. Pat. No. 3,976,596 includes a metal such as rhodium or iridium symmetrically bonded to the pentagonal face of a dicarbollide ligand. The compound further contains two triphenylphosphine ligands and one hydrogen ligand bound to the metal at the remaining ligand sites. This particular type of metallocarborane catalyst has been found to be relatively reactive when used as a homogenous catalyst.

U.S. Pat. No. 4,062,883 issued to Hawthorne et al. on Dec. 13, 1977 discloses a heterogeneous metallocarborane catalyst based on their original metallocarborane which is bound to a polymer support by a carbon-boron bond. By attaching a polymeric support to the carborane cage or dicarbollide ligand, this second patent issued to Hawthorne et al. discloses the conversion of the original homogeneous metallocarborane catalyst into a heterogeneous catalyst which could be more easily removed from solution.

Although both of the above-discussed metallocarborane catalysts are satisfactory it would be very desirable if there could be developed metallocarborane catalysts which are even more highly reactive.

SUMMARY OF THE INVENTION

We have found that using our previously developed metallocarboranes, the rate of hydrogenation is proportional to the reciprocal of the concentration of added triphenylphosphine. We concluded, based on this observation, that there was a possibility that catalytic reactivity would be increased if the triphenylphosphine was removed or displaced in some manner which would provide access to the transition metal of our metallocarboranes.

We have surprisingly found that if we replace one of the triphenylphosphine ligands in our carborane catalysts, discussed above, with a particular chelating alkene group, a novel metallocarborane catalyst is produced which is extraordinarily reactive. This alkene group has from three to five carbons and an olefin radical located in the alpha position. The alkene group may be unsubstituted, i.e. all of the carbon atoms are bound with hydrogen, or substituted, i.e. one or more of the hydrogen atoms are replaced with a lower alkyl and/or aryl group particularly one having six carbon atoms in the ring such as phenyl or benzyl.

The catalyst may be represented as:

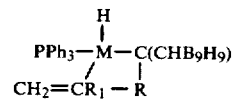

where M is a transition metal such as rhodium, iridium or ruthenium, R is

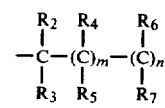

where m is 0 or 1 and when m is 1, n is 0 or 1 and when m is 0, n is 0 each of R1, R2, R3, R4, R5, R6 and R7 is either hydrogen, a lower alkyl or aryl group.

The alkene chain ($CH_2=CR_1-R$) is bound at its unsaturated end to the transition metal and bound at the other (hereinafter "second") end to one of the dicarbollide ligand carbons. This chelating or bridging lower alkene group may be from three to five carbon atoms with the chain terminating in a vinyl or olefin group at its first end. As noted the alkene chain may be substituted with a lower alkyl or aryl substituted at all carbons except the alpha carbon atom.

The new alkene carborane catalyst as described above is particularly useful in catalyzing hydrogenation, hydroformylation and isomerization reactions. The new catalyst is believed to be among the most active catalysts reported to date in the field and is of high value to the petrochemical industry.

The high reactivity of the new catalyst in accordance with the present invention may be due to the in situ irreversible hydrogenation of the alkene side chain under the conditions for alkene hydrogenation to produce an open coordination site on the transition metal. As discussed hereinbefore, this effective removal of a triphenylphosphine ligand from the transition metal may provide increased access to the transition metal which may be the reason for the greatly increased resultant increased catalytic activity.

The new catalyst is not only a highly reactive homogenous carborane catalyst, but may also be bound to suitable polymer supports as demonstrated in U.S. Pat. No. 4,062,883 to provide a highly reactive heterogeneous metallocarborane catalyst.

The above-discussed and many other features and attendant advantages of the present invention will become apparent from the following detailed description of preferred embodiments when considered in conjunction with the accompanying drawing.

BRIEF DESCRIPTION OF THE DRAWINGS

The drawing is a representation of the structure of a preferred alkene-carborane catalyst in accordance with the present invention.

DETAILED DESCRIPTION OF A PREFERRED EXEMPLARY EMBODIMENT

As previously discussed, the carborane catalysts of the present invention are an improvement on the hydrido metallocarborane catalytic compounds disclosed and discussed in U.S. Pat. No. 3,976,596 issued to Hawthorne et al. on Aug. 24, 1976. The contents of this patent are hereby incorporated by reference. This patent discloses carborane catalysts which basically include a transition metal atom bound to the pentagonal face of a dicarbollide ligand. The three remaining ligand sites are filled by two triphenylphosphine groups and a hydrogen atom. This prior catalyst may be represented as $$\begin{array}{c} H \\ | \\ PPh_3\text{---}M\text{---}C_2B_9H_{10}R' \\ | \\ PPh_3 \end{array}$$

where M is either rhodium or iridium and R' is a general designation for substances including $CH_3$—, $Ph$—, $CH_3CH_2OCH_2$— and other aryl and alkyl moieties attached to one of the carbons on the dicarbollide ligand. In this particular family of catalysts, the dicarbollide ligand ($C_2B_9H_{10}R$) may be formed in either of two isomers depending upon placement of the carbon atoms within the dicarbollide ligand or carborane cage. The present invention has application to both isomers; however, the following description deals only with the isomer where the carbon atoms are adjacent to each other i.e. the 1,2—$MC_2B_9H_{11}$ isomer. As previously discussed, the catalyst of the present invention involves substitution of an alkene chain for one of the triphenyl phosphine groups of the above represented compound. This results in the formation of the catalyst in accordance with the present invention having a lower alkene group which as shown in the formula representation and FIG. 1 is bonded not only to the metal atom but also to one of the carbon atoms in the dicarbollide ligand.

A particularly preferred catalyst in accordance with the present invention is shown in FIG. 1. This catalyst includes an unsubstituted butenyl side chain as the alkene group. In the preferred catalyst shown in FIG. 1, M is rhodium, m is 1 and n is 0 and each of R1, R2, R3, R4 and R5 is hydrogen. This carborane compound may be characterized as

[closo-1,3-u-($\eta^2$-2-3,4-buten-1-yl)-3-H-3-PPh$_3$-3,1,2-RhC$_2$B$_9$H$_{10}$]

which will be hereafter referred to as complex I.

Preparation of complex I is shown diagrammatically as follows:

4-(o-carboranyl)-but-1-ene

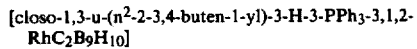

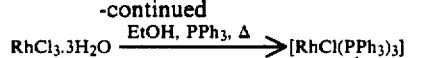

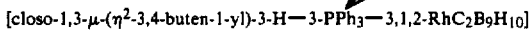

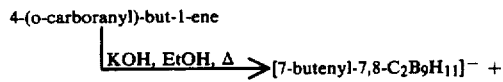

[closo-1,3-μ-($\eta^2$-3,4-buten-1-yl)-3-H—3-PPh$_3$—3,1,2-RhC$_2$B$_9$H$_{10}$]

As shown in the above diagram when a methanol solution of [RhCl(PPh$_3$)$_3$] was allowed to react with either the potassium or cesium salt of [7-butenyl-7,8-C$_2$B$_9$H$_{11}$] under an inert atmosphere a high yield (greater than 90%) of complex I was obtained. Complex I may be recrystallized from dichloromethane-ethanol under an inert atmosphere.

An example of preparation of Complex I in accordance with the above diagrammatic synthesis is as follows:

Preparation of 4-(O-carboranyl)-but-1-ene [1-(CH$_2$=CHCH$_2$CH$_2$)1,2-C$_2$B$_{10}$H$_{11}$].

A 500 ml three-neck round bottom flask was equipped with a magnetic stirrer, an addition funnel and a reflux condenser with a nitrogen inlet. The system was flushed with nitrogen, a solution of 32.0 g (222 mmol) of 1,2-C$_2$B$_{10}$H$_{12}$ in 50 ml of benzene was placed in the flask and 233 mmol of phenyl lithium in benzene solution was placed in the addition funnel. The stirred carborane solution was brought to reflux and the phenyl lithium slowly added. After 3 hours, 34.4 g (255 mmol) of 4-bromobut-1-ene was slowly added via the addition funnel and heating continued for 10 hours. The solution was then cooled and carefully hydrolyzed with water, and the benzene layer was separated and dried over anhydrous MgSO4. The MgSO$_4$ was separated by filtration, the benzene removed in vacuo and unreacted 1,2-C$_2$B$_{10}$H$_{12}$ removed from the resultant brown viscous oil by sublimation at 1 torr at 40° C. The brown oil was then repeatedly distilled at 1 torr to yield 35.2 g of a low-melting, white solid, 1-(CH$_2$=CHCH$_2$CH$_2$)-1,2-C$_2$B$_{10}$H$_{11}$ (m.p. 45°–6° C.) (80%).

The cesium salt of [7-butenyl-7,8-C$_2$B$_9$H$_{11}$] (Cs$^+$[7-(CH$_2$=CHCH$_2$CH$_2$)-7,8-C$_2$B$_9$H$_{11}$]$^-$) was then prepared as follows. A three-neck 100 ml round bottom flask equipped with a magnetic stirrer and reflux condenser with nitrogen inlet, was charged with 1.00 g (5.0 mmol) of 1-(CH$_2$=CHCH$_2$CH$_2$)-1,2-C$_2$B$_{10}$H$_{11}$, 0.92 g (16.4 mmol) of KOH and 45 ml of degassed ethanol. The solution was then refluxed for 12 hours. After cooling excess CO$_2$ was bubbled through the solution, the precipitated KHCO$_3$ removed by filtration and washed with ethanol and diethyl ether. The washings were combined with the filtrate and the solvent removed in vacuo. The resulting oil was dissolved in 200 ml of water and filtered through Celite. A 20 ml saturated aqueous solution of CsCl was slowly added to the filtrate precipitating a white solid. The solution was heated until the white solid completely dissolved and allowed to cool slowly giving white crystals which were collected and dried in vacuo to yield 1.13 g of Cs$^+$[7-(CH$_2$=CHCH$_2$CH$_2$)-7,8-C$_2$B$_9$H$_{11}$]$^-$ (m.p. 225°–8° C.).

Complex I was then prepared as follows. A 500 ml Schlenk flask equipped with a reflux condenser with nitrogen inlet, a magnetic stirrer and a septum on the side arm was charged with 0.652 g. (2.03 mmol) of Cs$^+$[7-(CH$_2$=CHCH$_2$CH$_2$)-7,8-C$_2$B$_9$H$_{11}$]$^-$, 1.343 g (1.45 mmol) of [RhCl(PPh$_3$)$_3$] and 250 ml of methanol. The solution was refluxed for 3 hours yielding a yellow precipitate which was collected, dried in vacuo and recrystallized from CH$_2$Cl$_2$-ethanol to give 0.730 g. of yellow crystals of Complex (I) (90%) (m.p. 170°-3° C. dec).

Complex I exhibits great stability in the solid state but is air sensitive in solutions of benzene, toluene and tetrahydrofuran (THF). The solutions are stable under an inert atmosphere such as nitrogen or argon.

To determine the chemical structure of complex I a number of tests were performed. From these tests it was found that the infrared spectrum of complex I contained absorptions characteristic of triphenylphosphine and the carborane moiety and an additional band (2060 cm-1) assigned to Rh-H. Elemental analysis, $^1$H and $^{31}$P nmr data confirmed the formulation as

[closo-1,3-$\mu$-($\eta^2$-2-3,4-buten-1-yl)-3-H-3-PPh$_3$-3,1,2-RhC$_2$B$_9$H$_{10}$].

In addition, as previously mentioned, an x-ray single crystal structure of complex I was determined to be that as shown in FIG. 1.

A variable temperature 200 MHz $^1$H nmr study of complex I was performed and the room temperature $^1$H nmr spectrum in CD$_2$C$_{12}$ was shown to result from the rapid interconversion of diastereomers. The spectrum exhibits resonances at 7.68, 7.63 and 7.47 assigned to the phenyl protons, a multiplet at 4.78, a doublet at 3.77 and a doublet at 3.75 due to the vinyl protons [H$_5$, H$_6$, H$_6$, respectively,

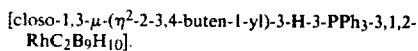

=24 Hz (trans)], a resonance at 4.26 assigned to the carboranyl C-H, resonances from 2.55 to 1.48 assigned to the alkyl protons of the butenyl group, and a doublet of doublets at −7.42 assigned to the rhodium hydride

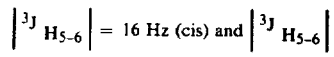

The 81 MHz $^{31}$P proton decoupled spectrum of complex I in CDC$_{13}$ displayed a doublet at 56.10 ppm (|$^J$Rh-P| =125 Hz), relative to D$_3$PO$_4$.

Complex I is formulated as a formal d$^6$ Rh(III) hydride with a triphenylphosphine occupying one coordination site and the chelating butene or -3,4-buten-1-yl side shain occupying another site with the rhodium symmetrically bound to the dicarbollide ligand as shown in FIG. 1.

It is possible that under a hydrogen atmosphere complex I undergoes irreversible hydrogenation of the alkenyl side chain to produce an open coordination site on the rhodium and in fact the facile hydrogenation of the side chain was demonstrated when complex I was exposed to hydrogen in a Tetrahydrofuran (THF) solution in the presence of excess triphenylphosphine. The product isolated in 90% yield was

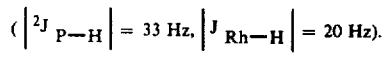

The increased catalytic activity of complex I is believed due to this surprising in situ hydrogenation of the alkenyl side chain.

Examples of practice utilizing complex I are as follows:

HYDROGENATION REACTIONS

Under a hydrogen atmosphere (1 atm) solutions of I catalyzed the hydrogenation of alkenes and alkynes as summarized in Tables I and II. A comparison of relative rates reveals that THF solutions of I exhibit faster rates than benzene or toluene solutions of I. The compound [Ir(1,5-cyclo-octadiene)P(i-Pr)$_3$(pyridine)]$^+$PF$_6^-$ reported by H. Felkin, T. Fillebeen-Khan, G. E. Morris and R. H. Crabtree in J. Organometal. Chem., 168, 183 (1970) is apparently the most active previously reported homogeneous hydrogenation catalyst. A CH$_2$C$_2$ solution of this catalyst (5.0×10$^{-4}$ M) and 3,3-dimethylbut-1-ene (0.5 M) displayed an initial rate of 2.3 mol sec-1/mol Ir for the hydrogenation of the alkene at 0° C. (P$_{H2}$=600 mm Hg). A THF solution of complex I (1.8×10$^{-4}$ M) and 3,3-dimethylbut-1-ene (0.13 M) displayed an initial rate of 8.9 mol sec-1/mol Rh at 0° C. for the reduction of the alkene when exposed to hydrogen (P$_{H2}$=705 mm Hg). Thus it can be seen that complex I is among the most active homogeneous hydrogenation catalysts yet discovered.

TABLE I

HYDROGENATION OF ALKENES AT 1 ATMOSPHERE PRESSURE

| mg I | Solvent | Temperature, °C. | Alkene | Initial Rate (mol · sec$^{-1}$/mol Rh) | % completion after 5 hrs |
|---|---|---|---|---|---|
| 25 | 25 ml benzene | 25 | 0.5 ml 3,3-dimethyl-but-1-ene | 4.3 × 10$^{-1}$ | 100 |
| 20 | 50 ml benzene | 11.8 | 0.4 ml 3,3-dimethyl-but-1-ene | 3.9 × 10$^{-1}$ | 100 |
| 21 | 50 ml toluene | 0 | 0.25 ml 3,3-dimethyl-but-1-ene | 1.6 × 10$^{-1}$ | 100 |
| 20 | 50 ml toluene | 0 | 0.225 ml pent-1-ene | 9.2 × 10$^{-2}$ | 100 |
| 3 | 30 ml THF | 0 | 0.5 ml 3,3-di-methyl-but-1-ene | 8.9 | 100 |
| 3 | 30 ml THF | 0 | 0.56 ml trimethylvinyl-silane | 2.3 × 10$^{-1}$ | 100 |
| 3 | 30 ml THF | 0 | 0.4 ml cyclohexene | 2.8 × 10$^{-3}$ | a |
| 25 | 30 ml THF | 25 | 0.345 ml styrene | 6.6 × 10$^{-2}$ | 100 |
| 100 | 30 ml THF | 25 | 0.403 ml n-butyl acrylate | 9.7 × 10$^{-4b}$ | 100 |

$^a$Reaction complete after 120 hrs.
$^b$After a short induction period

TABLE II

HYDROGENATION OF ALKYNES AT 1 ATMOSPHERE PRESSURE IN 30 ml OF THF AT 25° C.

| mg 1 | ALKYNE | PRODUCTS AFTER 18 HRS. | INITIAL RATE (mol . sec$^{-1}$/mol Rh) |
|---|---|---|---|
| 50 | 0.276 ml 3,3-dimethyl-but-1-yne | 78% neohexane, 17% 3,3-dimethylbut-1-ene | $7.4 \times 10^{-3}$ |
| 50 | 0.148 ml phenyl-acetylene | 100% ethylbenzene | $1.5 \times 10^{-1}$ |

HYDROFORMYLATION REACTIONS

Under an atmosphere of 50% hydrogen and 50% carbon monoxide THF solutions of complex I were found to catalyze the hydroformylation of hex-1-ene and 3,3-dimethylbut-1-ene. The results are summarized in Table III.

TABLE III

HYDROFORMYLATION OF ALKENES AT 1 ATMOSPHERE PRESSURE IN THF

| mg 1 | TEMPERATURE, °C. | ALKENE | PRODUCTS AFTER 120 HRS. |
|---|---|---|---|
| 42$^a$ | 25 | 0.4 ml 3,3-di-methyl-but-1-ene | 40% 4,4-dimethylvaleraldehyde, 45% 3,3-dimethylbut-1-ene 15% neohexane |
| 25$^b$ | 40 | 5.0 ml 3,3-di-methyl-but-1-ene | 74% 4,4-dimethylvaleraldehyde, 24% 3,3-dimethylbut-lene 2% neohexane |
| 100$^c$ | 40 | 1.9 ml hex-1-ene | 45.5% heptaldehyde, 16.8% 2-methylhexaldehyde, 28.6% hex-1-ene, 9.2% hexane |

$^a$In 28 ml THF
$^b$In 50 ml THF
$^c$In 30 ml THF

ISOMERIZATION REACTIONS

A THF solution of complex I ($4.5 \times 10^{-3}$ M) catalyzed the isomerization of hex-1-ene (4 M) at 25° C. After 120 hours the reaction mixture contained 0.25% hex-1-ene, 67% trans-hex-2-ene, 24% cis-hex-2-ene, 2.5% trans-hex-3-ene and 6.4% cis-hex-3-ene.

The above experiments show that the catalysts of this invention are useful for the hydrogenation, hydroformylation and isomerization of various substrates. The very high catalytic activity of complex I makes it of great value to the petrochemical industry.

As indicated in the above examples, the alkene-carborane catalysts of the present invention are excellent homogeneous catalysts in a suitable solvent such as THF, benzene or toluene. This new family of catalysts may be also used as heterogeneous catalysts to provide easier separation from solution.

To prepare a heterogeneous catalyst based on the new alkenecarborane catalyst of the present invention, a suitable polymer support such as chloromethylated polystyrene is preferably attached to the catalyst at the B(6) boron of the dicarbollide ligand. Preparation and use of polymer bound heterogeneous carborane catalysts is known and has been demonstrated and disclosed in U.S. Pat. No. 4,062,883, issued to Hawthorne et al. on Dec. 13, 1977. The contents and disclosure of this patent is hereby incorporated by reference.

Having thus described exemplary embodiments of the present invention, it should be noted by those skilled in that art that the within disclosures are exemplary only and that various other alternatives, adaptions and modifications may be made within the scope of the present invention. Accordingly, the present invention is not limited to the specific embodiments as illustrated herein.

What is claimed is:

1. A metallocarborane compound having the formula

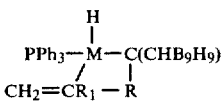

where M is a metal selected from the group consisting of Rhodium, Iridium and Ruthenium and

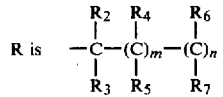

where m is 0 or 1 and when m is 1 n is 0 or 1 and when m is 0 n is 0, and wherein each of $R_1$, $R_2$, $R_3$, $R_4$, $R_5$, $R_6$, and $R_7$ is hydrogen, lower alky or aryl.

2. A metallocarborane compound according to claim 1 wherein M is Rhodium, and each of $R_1$, $R_2$, $R_3$, $R_4$ and $R_5$ is hydrogen.

3. A metallocarborane compound according to claim 2 wherein m is 1 and n is 0.

4. A metallocarborane catalytic solution comprising:
the metallocarborane compound according to claim 1;
and
a solvent for said metallocarborane compound.

5. A metallocarborane catalytic solution comprising: the metallocarborane compound of claim 2; and a solvent for said metallocarborane compound.

6. A metallocarborane catalytic solution comprising: the metallocarborane compound of claim 3; and a solvent for said metallocarborane compound.

7. A metallocarborane catalytic solution according to claim 4, claim 5 or claim 6 wherein said solvent is selected from the group consisting of tetrahydrofuran, benzene and toluene.

8. A metallocarborane catalyst according to claim 1, claim 2 or claim 3 wherein said metallocarborane catalyst is bound to a polymer support.

* * * * *